United States Patent
Doki et al.

(10) Patent No.: US 10,732,132 B2
(45) Date of Patent: Aug. 4, 2020

(54) RADIATION PHASE CONTRAST IMAGING DEVICE

(71) Applicants: Shimadzu Corporation, Kyoto (JP); OSAKA UNIVERSITY, Suita-shi (JP)

(72) Inventors: Takahiro Doki, Kyoto (JP); Koichi Tanabe, Kyoto (JP); Toshinori Yoshimuta, Takatsuki (JP); Kenji Kimura, Kyoto (JP); Akihiro Nishimura, Kyoto (JP); Taro Shirai, Kyoto (JP); Satoshi Sano, Kyoto (JP); Akira Horiba, Kyoto (JP); Takayoshi Shimura, Suita (JP); Heiji Watanabe, Suita (JP); Takuji Hosoi, Suita (JP)

(73) Assignees: Shimadzu Corporation, Nishinokyo-Kuwabaracho, Nakagyo-ku, Kyoto-shi, Kyoto (JP); OSAKA UNIVERSITY, Yamadaoka, Suita-shi, Osaka (JP)

( * ) Notice: Subject to any disclaimer, the term of this patent is extended or adjusted under 35 U.S.C. 154(b) by 1 day.

(21) Appl. No.: 16/081,249

(22) PCT Filed: Feb. 22, 2017

(86) PCT No.: PCT/JP2017/006625
§ 371 (c)(1),
(2) Date: Aug. 30, 2018

(87) PCT Pub. No.: WO2017/159255
PCT Pub. Date: Sep. 21, 2017

(65) Prior Publication Data
US 2019/0056336 A1    Feb. 21, 2019

(30) Foreign Application Priority Data

Mar. 14, 2016    (JP) .................... 2016-049964

(51) Int. Cl.
*G01N 23/04*    (2018.01)
*G01N 23/041*    (2018.01)
(Continued)

(52) U.S. Cl.
CPC ......... *G01N 23/041* (2018.02); *A61B 6/4233* (2013.01); *A61B 6/4291* (2013.01);
(Continued)

(58) Field of Classification Search
CPC ..... A61B 6/484; A61B 6/4233; A61B 6/4291; G01N 23/041; G01N 23/20075; G01K 1/06; G21K 2201/06
See application file for complete search history.

(56) References Cited

U.S. PATENT DOCUMENTS

2014/0079184 A1* 3/2014 Das .................. A61B 6/484
378/62
2014/0286475 A1* 9/2014 Nakamura ............... G01T 1/16
378/51
2015/0131783 A1    5/2015 Sato

FOREIGN PATENT DOCUMENTS

JP    2009-195349 A    9/2009
JP    2012-016370 A    1/2012
(Continued)

OTHER PUBLICATIONS

International Search Report for PCT application PCT/JP2017/006625 dated May 23, 2017.
(Continued)

Primary Examiner — Kiho Kim
(74) Attorney, Agent, or Firm — Muir Patent Law, PLLC

(57) ABSTRACT

[PROBLEM TO BE SOLVED] To provide a radiation phase contrast imaging device having a small device configuration [SOLVING MEANS] The present invention focused on the findings that the distance between the phase grating 5 and (Continued)

the FPD 4 does not need to be the Talbot distance. The distance between the phase grating 5 and the FPD 4 can be more freely set. However, a self-image cannot be detected unless the self-image is sufficiently magnified with respect to the phase grating 5. The degree on how much the self-image is magnified on the FPD 4 with respect to the original phase grating 5 is determined by a magnification ratio X2/X1. Therefore, in the present invention, the magnification ratio is set to be the same as the magnification ratio in a conventional configuration. With this, even if the distance X2 between the radiation source 3 and the FPD 4 is reduced, a situation in which the self-image cannot be detected by the FPD 4 due to the excessively small size thereof does not occur.

11 Claims, 5 Drawing Sheets

(51) Int. Cl.
*A61B 6/00* (2006.01)
*G21K 1/06* (2006.01)
*G01N 23/20* (2018.01)

(52) U.S. Cl.
CPC ....... *A61B 6/484* (2013.01); *G01N 23/20075* (2013.01); *G21K 1/06* (2013.01); *G21K 2201/06* (2013.01)

(56) References Cited

FOREIGN PATENT DOCUMENTS

| | | |
|---|---|---|
| JP | 2013-122487 A | 6/2013 |
| JP | 2015-047306 A | 3/2015 |
| JP | 2015-118081 A | 6/2015 |

OTHER PUBLICATIONS

Written Opinion of the International Searching Authority for PCT application PCT/JP2017/006625 dated May 23, 2017.
Notification of Reasons for Refusal dated Jan. 14, 2020 for corresponding Japanese Patent Application No. JP 2018-505386, submitted with a machine translation.

* cited by examiner

RADIATION PHASE CONTRAST IMAGING DEVICE

TECHNICAL FIELD

The present invention relates to a radiation phase contrast imaging device capable of imaging an internal structure of an object utilizing a phase contrast of radiation transmitted through the object.

BACKGROUND ART

Conventionally, various devices have been conceived as a radiation imaging device for imaging an internal structure of an object by making radiation transmit through the object. A commonly-used radiation imaging device is configured to image a radiation projection image by irradiating radiation to an object to make the radiation transmit through the object. In such a projection image, contrasting density appears depending on the ease of permeation of radiation, which represents the internal structure of the object.

With such a radiation imaging device, only objects having a property capable of absorbing radiation to some extent can be imaged. For example, soft biological tissues hardly absorb radiation. Even if it is tried to image such a tissue with a general device, nothing is reflected on the projection image. When trying to image the internal structure of an object that does not absorb radiation as described above, there is a theoretical limit in a general radiation imaging device.

Under the circumstances, a radiation phase contrast imaging device configured to image an internal structure of an object by utilizing a phase contrast of transmitted radiation has been proposed. Such a device is configured to image an internal structure of an object by using Talbot interference.

Talbot interference will be described. From the radiation source 53 shown in FIG. 9, phase-aligned radiation is irradiated. When making the radiation transmit through a phase grating 55 which is in a streak form, the image of the phase grating 55 appears on the projection plane which is apart from the phase grating 55 by a predetermined distance (Talbot distance). This image is called a self-image. Note that this self-image is not just a projection image of the phase grating 55. The self-image is generated only at the position where the projection plane is separated from the phase grating 55 by the Talbot distance. The self-image is configured by the interference fringes caused by interference of light. The reason that the self-image of the phase grating 55 appears at the Talbot distance is that the phase of radiation generated from the radiation source 53 is aligned. When the phase of radiation is disturbed, the self-image appearing at the Talbot distance is also disturbed.

The radiation phase contrast imaging device is configured to image an internal structure of an object by utilizing the self-image disturbance. It is assumed that the object is placed between the radiation source and the phase grating 55. Since this object hardly absorbs radiation, most of the radiation incident on the object exits to the phase grating 55 side.

The radiation has not passed through the object completely as it is. The reason is that the phase of the radiation changes while passing through the object. The radiation exited the object passes through the phase grating 55 with the phase changed. The observation of the radiation on the projection plane arranged at the Talbot distance shows disturbances in the self-image of the phase grating 55. The degree of disturbance of the self-image represents the radiation phase change.

The specific magnitude of the phase change of the radiation that passed through the object changes depends on where the radiation passed through the object. If the object has a homogeneous configuration, the change of the radiation phase remains the same no matter where the radiation passed through the object. In general, however, an object has some internal structure. When radiation is made to pass through such an object, the phase change does not remain the same.

Therefore, when the phase change is known, the internal structure of the object can be grasped. The phase change can be known by observing the self-image of the phase grating 55 at the Talbot distance. The detection of such a self-image is performed by a radiation detector. The radiation detector has a detection surface that detects radiation. By projecting a self-image on this detection surface, the radiation detector can perform imaging of the self-image (see, for example, Patent Document 1).

The multi-slit shown in FIG. 9 is provided for the purpose of increasing the coherency of the X-ray beam. In the radiation phase contrast imaging device, it can be considered that X-rays are irradiated from this multi-slit. This is because highly coherent X-rays emitted from the multi-slit are sources used for the phase contrast imaging. The position of the phase grating 55 and the position of the radiation detector are determined on the basis of the multi-slit.

The phase grating 55 is a grating with an extremely fine pattern. Therefore, the self-image also becomes fine. The radiation emitted from the radiation source 53 spreads radially. Therefore, as the distance between the phase grating 55 and the radiation detector is increased, the self-image is magnified and becomes easy to detect. This is because that the spatial resolution of the radiation detector has a limit.

That is, in a conventional configuration, the device configuration is that the radiation source 53, the phase grating 55, and the radiation detector are placed in predetermined positions. The positional relationship of these parts is determined as follows. First, it is necessary that the distance between the phase grating 55 and the radiation detector is a predetermined Talbot distance. Otherwise the self-image does not appear on the detection surface of the radiation detector. In addition, it is necessary that the self-image is an image magnified to a certain extent with respect to the phase grating 55. Otherwise, the self-image is too fine to be detected with the radiation detector.

PRIOR ART

Patent Document

Patent Document 1: International Patent Application Publication No. 2009104560

SUMMARY OF THE INVENTION

Problems to be Solved by the Invention

However, the conventional radiation phase contrast imaging device has the following problems.

That is, in a conventional radiation phase contrast imaging device, the entire device becomes large. The radiation detector should be arranged at a position separated from the phase grating 55 by a Talbot distance. This is because the self-image of the phase grating 55 appears at a position separated from the phase grating 55 by the Talbot distance.

However, since the radiation phase contrast imaging device is a device including the phase grating 55 and the radiation detector, as the radiation detector is separated from the phase grating 55, the device itself becomes huge. This becomes an obstacle when attempting to make the device compact.

The present invention has been made in view of the aforementioned circumstances, and an object of the present invention is to provide a radiation phase contrast imaging device with a small device configuration.

Means for Solving the Problems

In order to solve the aforementioned problems, the present invention has the following configuration.

That is, the radiation phase contrast imaging device according to the present invention includes:

a radiation source configured to irradiate radiation;

a grating in which absorbers extending in one direction configured to absorb the radiation are arranged in a direction orthogonal to the one direction; and a detection portion configured to detect a self-image of the grating caused by a Talbot interference at a detection surface for detecting the radiation, wherein when a distance from the radiation source to the detection portion is X2 and a distance from the radiation source to the grating is X1, X2−X1 is set to a distance different from the Talbot distance in a state in which a magnification ratio X2/X1 showing how much the self-image of the grating which appears at the detection portion in a device configuration in which X2−X1 is set to the Talbot distance is magnified with respect to the grating is maintained constant.

[Functions and Effects] According to the present invention, it is possible to provide a radiation phase contrast imaging device with a small device configuration. According to the present invention, it focuses on the findings that there is no need to set a distance between a grating and a detection portion to a Talbot distance. The distance between the grating and the detection portion can be set more freely. However, the self-image cannot be detected unless the self-image is sufficiently magnified with respect to the grating. The degree on how the self-image is magnified on the detection portion with respect to the original grating is determined by a magnification ratio X2/X1. Therefore, in the present invention, the magnification ratio is set to be the same as the magnification ratio in a conventional configuration. With this, even if the distance X2 between the multi-slit and the detection portion is reduced, a situation in which the self-image cannot be detected by the detection portion due to the excessively small size thereof does not occur.

Further, X2−X1 may be set to a distance different from a Talbot distance by setting the magnification ratio X2/X1 between the upper and the lower limits. Here, the upper limit of the magnification ratio is a value at which the dark line located at the end of the self image having the stripe pattern consisting of dark lines extends by ½ of the width of the detection element and the lower limit is a value at which the dark line narrows by ½ of the width of the detection element. The dark line at the end of the self image has the largest positional deviation against the variation of the magnification ratio.

[Functions and Effects] Even if X2/X1 is not exactly set to an ideal value, the effects of the present invention will not be impaired and the influence does not appear much in capturing a self-image.

Further, in the radiation phase contrast imaging device described above, it is more preferable that the distance X1 from the radiation source to the grating and the distance X2 from the radiation source to the detection portion satisfy a relationship of:

$$P1(X2/X1)=N \cdot Pd$$

where N is an integer, P1 is an array pitch of the absorber in the grating, and Pd is an array pitch of the detection element arranged on the detection surface of the detection portion.

[Functions and Effects] According to the present invention, it is possible to provide a radiation phase contrast imaging device with a small device configuration. That is, there is a relationship P1 (X2/X1)=N·Pd between the distance X1 from the multi-slit to the grating and the distance X2 from the multi-slit to the detection portion. Among them, X2/X1 is called a magnification ratio and is an index showing how much the self-image of the grating is magnified on the detection portion. After determining the magnification ratio X2/X1 so as to satisfy the above expression using the array pitch P1 of the absorber in the grating and the array pitch Pd of the detection elements arranged on the detection surface of the detecting portion, X2 and X1 are determined so as to satisfy the magnification ratio and then the array pitch of the dark line configuring the self-image can be an integer multiple of the array pitch of the detection elements of the detection portion. With this, a radiation phase contrast imaging device capable of assuredly detecting a self-image can be provided. Even in cases where the magnification ratio X2/X1 is set to be constant, by reducing the distance X1, the distance X2 can be reduced. This makes it possible to reduce the detection portion. Further, the device configuration of the radiation phase contrast imaging device can also be reduced.

Further, in the above-described radiation phase contrast imaging device, it is more desirable that X2−X1 be shorter than the Talbot distance.

[Functions and Effects] According to the above-described configuration, the device configuration of the radiation phase contrast imaging device can also be reduced.

Effects of the Invention

There is a relationship P1 (X2/X1)=N·Pd between the distance X1 from the multi-slit to the grating and the distance X2 from the multi-slit to the detection portion in the present invention. In the present invention, the magnification ratio X2/X1 is determined so as to satisfy the above expression according to the array pitch P1 of the absorber in the grating and the array pitch Pd of the detection elements arranged on the detection surface of the detection portion and, based on this, X2 and X1 are determined. With this, a radiation phase contrast imaging device capable of assuredly detecting a self-image can be provided. Even in cases where the magnification ratio X2/X1 is set to be constant, by reducing the distance X1, the distance X2 can be reduced. Therefore, according to the present invention, it is possible to reduce the detection portion. Further, the device configuration of the radiation phase contrast imaging device can also be reduced.

DESCRIPTION OF PREFERRED EMBODIMENTS

Example 1

The radiation phase contrast imaging device according to the present invention is an imaging device for generating a transparent image by using Talbot interference. Note that X-rays correspond to the radiation of the present invention. An FPD is an abbreviation of a flat panel detector.

Figure 1:
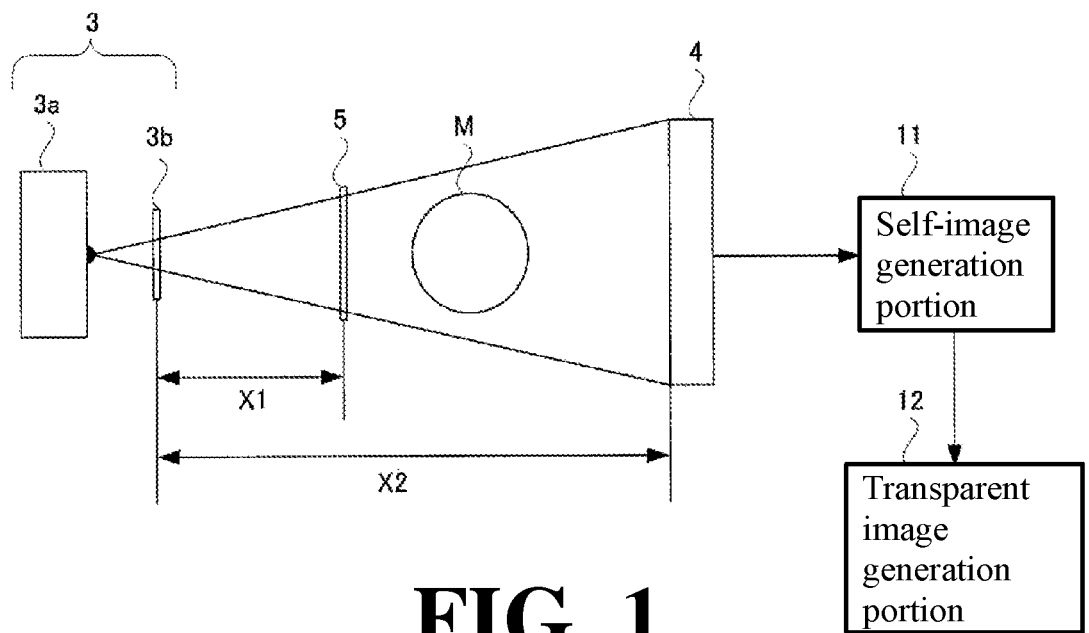
FIG. 1 is a functional block diagram explaining an overall configuration of a radiation phase contrast imaging device according to Example 1.
Figure 9:
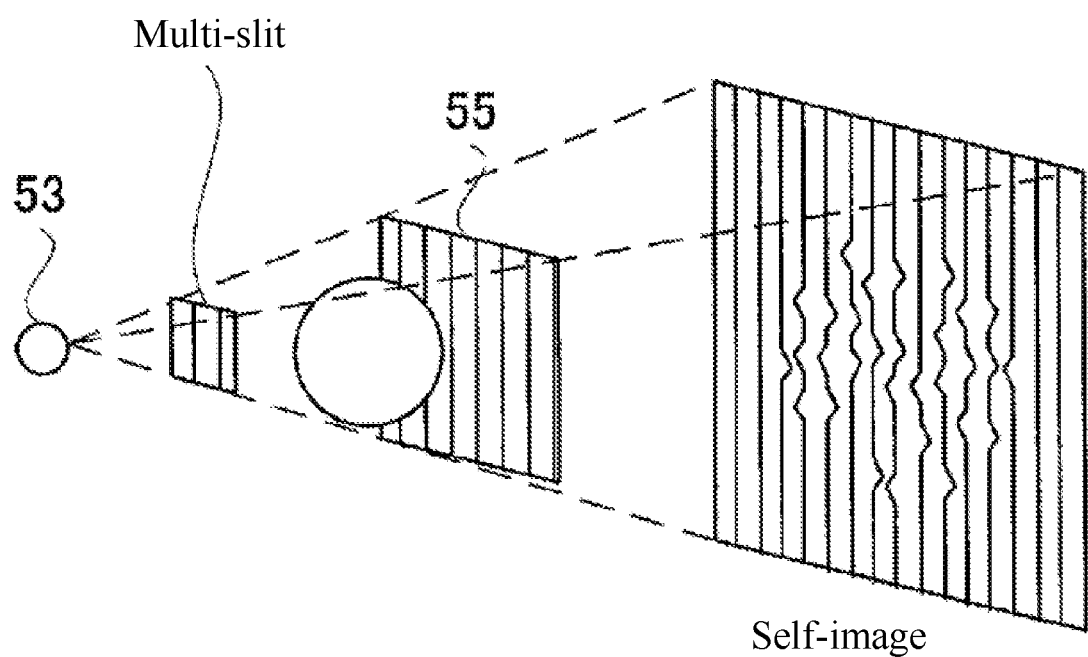
FIG. 9 is a schematic diagram explaining a conventional radiation phase contrast imaging device.

FIG. 1 is a functional block diagram illustrating a configuration of a radiation phase contrast imaging device according to the present invention. As shown in FIG. 1, a radiation source 3 according to the present invention is equipped with a positive electrode 3a with which electrons collide and a multi-slit 3b on which X-rays irradiated from the positive electrode 3a are incident. The positive electrode 3a is a target of electrons, and X-rays are generated when high-speed electrons collide with the positive electrode 3a. X-rays are generated at a single focal point p. The radiation source 3 irradiates radiation. Although the radiation source 3 is configured to output X-rays of a specific wavelength, it also irradiates a plurality of types of radiation having different wavelengths. A subject M is placed between phase grating 5 and the FPD 4. Further, as shown in FIG. 9, it may be configured such that the subject is placed between the multi-slit 3b and the phase grating 5.

Figure 2:
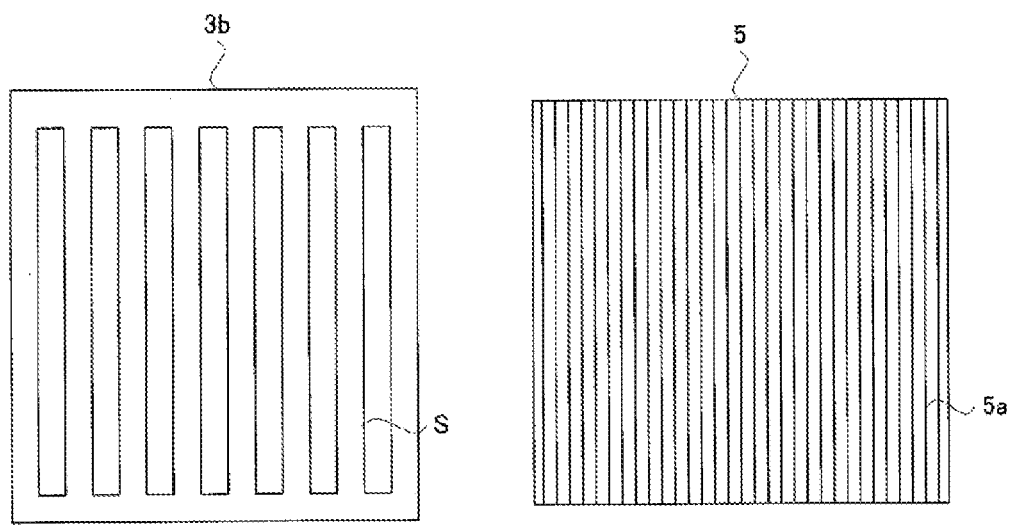
FIG. 2 is a plan view explaining each part configuring the radiation phase contrast imaging device according to Example 1.

The fan-shaped X-ray beam emitted from the positive electrode 3a is incident on the multi-slit 3b. The multi-slit 3b is made of a material, such as, e.g., gold, which is easy to process, and has a thickness to the extent that X-rays are not allowed to pass through. The left side of FIG. 2 illustrates the multi-slit 3b of the present invention. The multi-slit 3b is configured such that slits S extending in the vertical direction Y are arranged in the lateral direction X. Each of the slits S is a through-hole of the multi-slit 3b. The slits S are arranged at equal intervals in the lateral direction X. In the multi-slit 3b, the slits S that allow transmission of radiation generated at a single generation point are arranged at a constant pitch in a direction orthogonal to the extending direction of the slit S, and radiation incident on the part where no slit S is provided is absorbed.

The X-ray beam generated at the positive electrode 3a passes through one of the slits S provided in the multi-slit 3b and exits from the multi-slit 3b. At this time, each of the X-ray beams that have passed through the slits S of the multi-slit 3b interferes, turns into an X-ray beam with high coherency, and goes to the phase grating 5 (see FIG. 1). Note that the phase grating 5 corresponds to the "grating" of the present invention.

The right side of FIG. 2 shows the phase grating 5. The phase grating 5 has a plurality of absorption lines 5a absorbing X-rays and extending in a linear manner. The absorption lines 5a are arranged at a predetermined pitch in a direction perpendicular to the extending direction. The X-ray beam emitted from the multi-slit 3b passes through the phase grating 5. At that time, a part of the X-ray beam is absorbed by the phase grating 5. The X-ray beam emitted from the phase grating 5 has a pattern in which a plurality of bright lines remained without being absorbed by the absorption lines 5a is arranged. Since the pitch of the absorption line 5a of the phase grating 5 is sufficiently small, interference occurs between bright lines. Due to this interference, a streak form image similar to the image of the phase grating 5 appears at a distance away from the phase grating 5 by the Talbot distance. It should be noted that this image is not just a shadow of the phase grating 5 but an interference fringe caused by interference. This image is called a self-image. The X-rays emitted from the phase grating 5 are directed to the FPD 4 (see FIG. 1). The FPD 4 is configured to detect a self-image of the phase grating 5 caused by the Talbot interference on the detection surface 4a for detecting the radiation. The absorption line 5a corresponds to the absorber of the present invention.

The FPD 4 is a direct conversion type X-ray detector. That is, the FPD 4 has a conversion layer for converting the X-rays into an electron and hole pair (charge carrier pair). The carriers generated in the conversion layer are captured by and accumulated in each of the detection elements 4p. When a signal for outputting a carrier is sent to the detection element 4p, the detection element 4p outputs the accumulated carrier as a detection signal. The fineness of this detection element 4p is a main factor determining the spatial resolution of the FPD 4. The smaller the detection element 4p, the better the spatial resolution of the FPD 4, so that it is possible to detect a finer structure. The conversion layer corresponds to the conversion portion of the present invention. The FPD 4 according to Example 1 does not have a configuration for detecting the fluorescence generated by the X-rays. Note that the FPD corresponds to the detection portion of the present invention.

The conversion layer of the FPD 4 is made of amorphous selenium, CdTe, CdZnTe or the like and has a property of absorbing incident X-rays and generating a carrier pair of an electron and a hole. The FPD 4 having such a conversion layer is called a direct conversion type. This means that X-rays are directly converted into carrier pairs. As a similar one, there is an indirect conversion type FPD. Such an FPD has a layer that absorbs X-rays and emits fluorescence and a layer that converts fluorescence into an electric signal.

Adoption of a direct conversion type FPD has an advantage that spatial resolution of detection can be improved. In the case of the indirect conversion type, even if it is attempted to detect fluorescence generated at a certain generation point, since the fluorescence spreads out from the generation point and is detected, it is not precisely known where the generation point is. Compared to this, in the case of the direct conversion type, when a carrier pair occurs at a certain generation point, the generated charge is attracted to the detection element 4p and accumulated, so it is comparatively easy to say where the generation point occurs.

Figure 3:
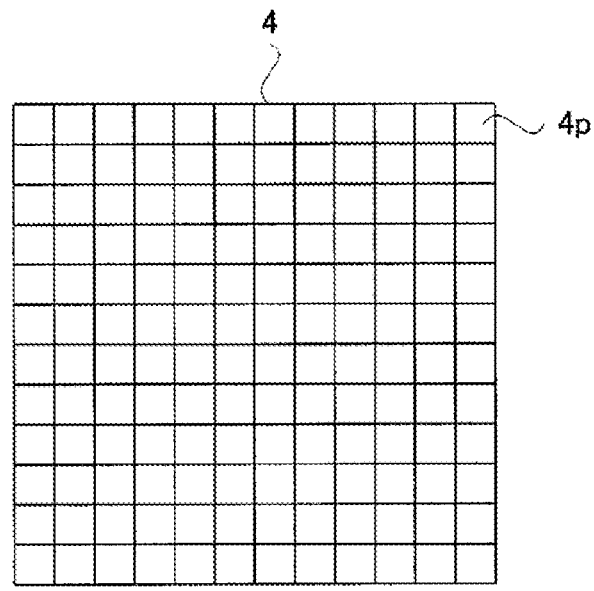
FIG. 3 is a plan view explaining each part configuring the radiation phase contrast imaging device according to Example 1.

FIG. 3 explains the configuration of the X-ray detection surface 4a of the FPD 4. The detection surface 4a of the FPD 4 has such a shape that the self-image of the rectangular phase grating 5 is reflected thereon. Therefore, the detection surface 4a of the FPD 4 has a rectangular structure like the phase grating 5. On the detection surface 4a of the FPD 4, rectangular detection elements are arrayed vertically and horizontally. The direction in which the absorption lines 5a of the phase grating 5 each extend corresponds to the vertical direction in which the detection elements 4p on the detection surface 4a of the FPD 4 are arranged and the direction in which the absorption lines 5a of the phase grating 5 are arranged is the lateral direction of the detection surface 4a of the FPD 4. In the phase grating 5, absorption lines extending in one direction configured to absorb X-rays are arranged in a direction orthogonal to the one direction.

Figure 4:
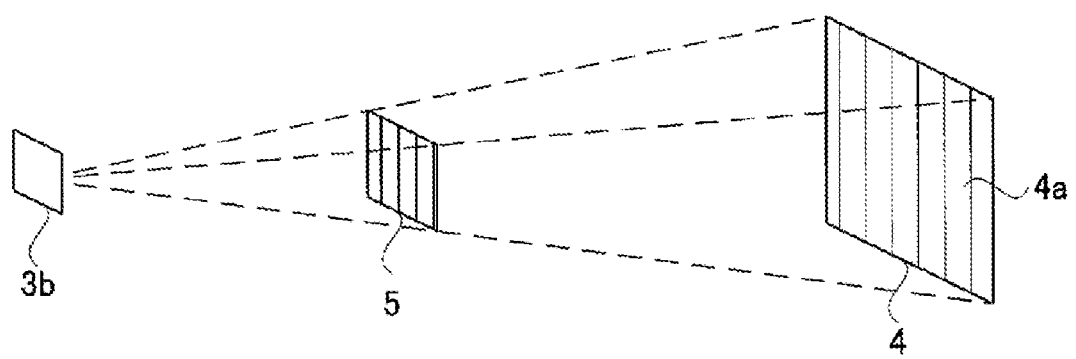
FIG. 4 is a schematic diagram explaining magnification of a self-image according to Example 1.

FIG. 4 explains how the X-ray beam emitted from the multi-slit 3b reaches the detection surface 4a of the FPD 4. The X-ray beam emitted from the multi-slit 3b radially spreads, passes through the phase grating 5, and reaches the FPD 4. Therefore, the self-image of the phase grating 5 is magnified until it reaches the FPD 4.

Most Characteristic Configuration of Present Invention

Figure 5:
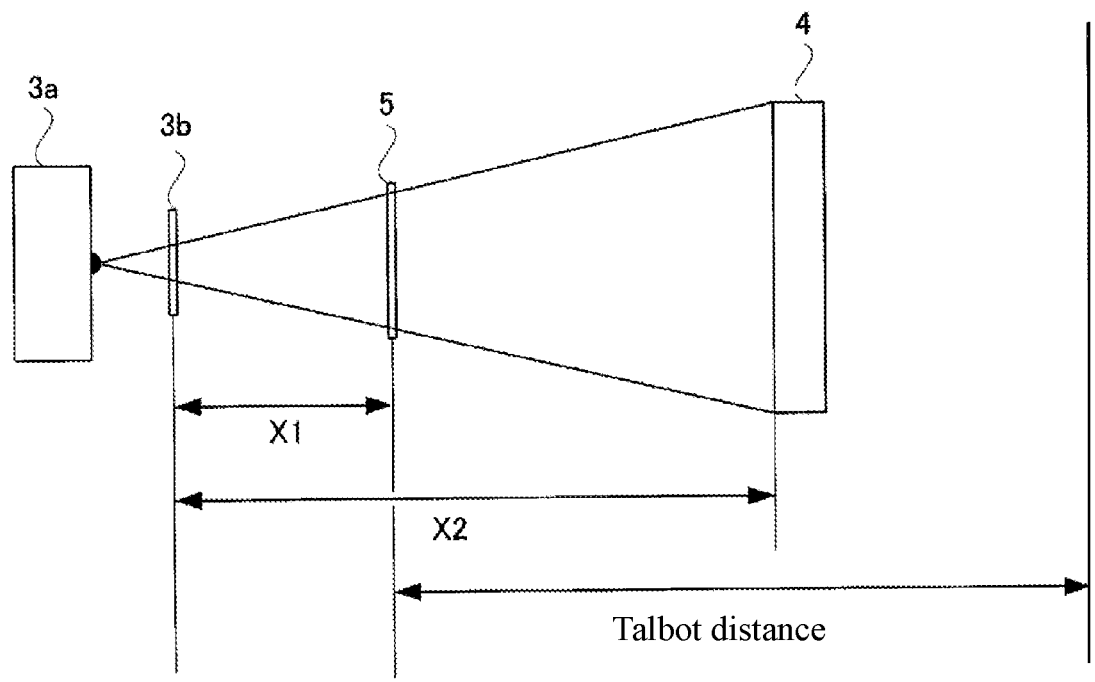
FIG. 5 is a schematic diagram explaining the positional relationship of each part according to Example 1.

FIG. 5 explains the most characteristic configuration of the present invention. That is, the distance between the phase grating 5 and the FPD 4 of the present invention is not set to a Talbot distance. Considering the principle of Talbot interference, unless the distance between the phase grating 5 and the FPD 4 is set to the Talbot distance, the self-image of the phase grating 5 will not appear on the detection surface 4a of the FPD 4. However, this is only a prediction derived from the principle of Talbot interference. In actual imaging, it is possible to obtain a sharp self-image sufficiently for phase contrast imaging without exactly setting the distance between the phase grating 5 and the FPD 4 to the Talbot distance. The distance between the phase grating 5 and the FPD 4 in the present invention is shorter than the Talbot distance. By doing this, the distance from the radiation source 3 to the FPD 4 becomes shorter, which makes the device compact by that.

Figure 6:
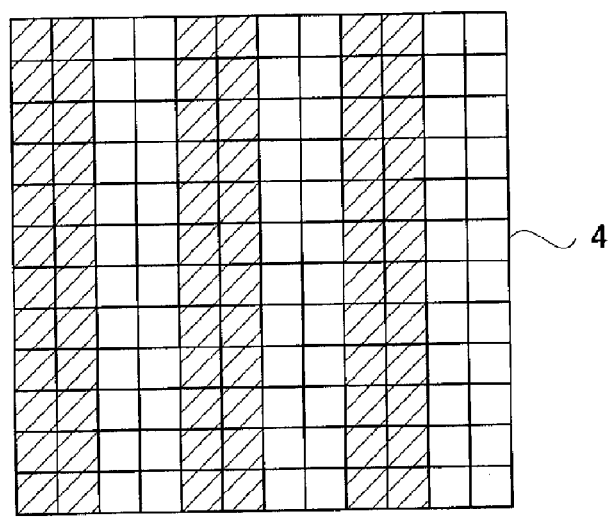
FIG. 6 is a schematic diagram explaining how a self-image appears in an FPD according to Example 1.

As shown in FIG. 5, the distance from the radiation source 3 (more precisely, the multi-slit 3b) to the phase grating 5 is X1, and the distance from the radiation source 3 (more precisely, the multi-slit 3b) to the FPD 4 is X2. Since there is a special relationship between the distance X1 and the distance X2, this point will be explained. FIG. 6 shows how the self-image of the phase grating 5 is projected onto the detection surface 4a of the FPD 4. The self-image looks like an image in which the streak form pattern of the phase grating 5 is magnified. The X-rays irradiated from the radiation source 3 spread radially, so the image is magnified. This magnification ratio is equal to X2/X1.

As shown in FIG. 6, in the device according to the present invention, the array pitch of the dark lines constituting the self-image is an integer multiple of the array pitch Pd of the detection elements of the FPD 4. By arranging the array pitch like this, the dark lines constituting the self-image do not protrude to the adjacent detection element side. The phase grating 5 and the FPD 4 can be aligned so that all of the dark lines fall within two detection element arrays. In this way, it is possible to accurately grasp the movement of the dark lines. This is because if the dark line is deviated from the center of the detection element, the detection result of the FPD 4 will differ between when the dark line is shifted to the right and when it is shifted to the left.

Figure 7:
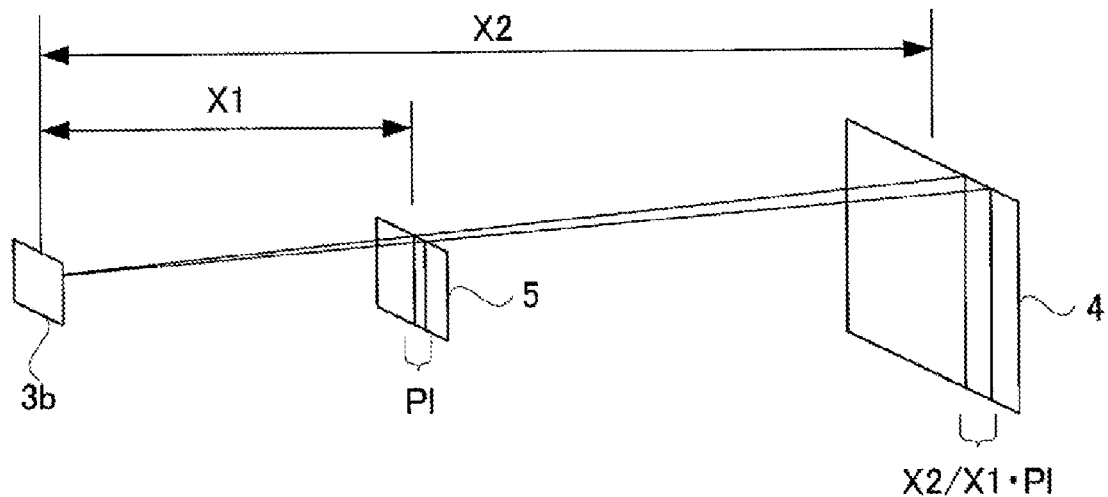
FIG. 7 is a schematic diagram explaining a relational expression according to Example 1.

FIG. 7 explains the condition that the array pitch of the dark lines constituting the self-image is an integer multiple of the array pitch Pd of the detection element of the FPD 4. Let P1 be the array pitch of the absorption lines 5a in the phase grating 5. The pattern of the streak form possessed by the phase grating 5 becomes a magnified self-image and is reflected on the detection surface of the FPD 4. The magnification ratio at this time is X2/X1. Therefore, the array pitch of the dark lines configuring the self-image is equal to P1 (X2/X1).

Therefore, in the device according to the present invention, the following relation is satisfied:

$$P1(X2/X1)=N \cdot Pd$$

where N is an integer. In the case shown in FIG. 6, N is set to 4. Therefore, adjacent dark lines configuring the self-image are separated by the width of four detection elements.

The magnification ratio X2/X1 in the aforementioned equation according to the present invention is the same as that of a conventional radiation phase contrast imaging device. The conventional radiation phase contrast imaging device denotes a configuration in which the distance from the phase grating 5 to the FPD 4 is a Talbot distance. In the radiation phase contrast imaging device of the present invention, the distance X2 between the phase grating 5 and the FPD 4 is the Talbot distance. In a device configuration in which the distance from the radiation source 3 to the phase grating 5 is X1, the distance X2−X1 is set to a distance different from the Talbot distance in a state in which the magnification ratio X2/X1 showing how much the self-image of the phase grating 5 appearing on the FPD 4 is magnified with respect to the phase grating 5 is kept constant.

There is the following merit in changing the device configuration so that the magnification ratio X2/X1 is set to be constant like in a conventional configuration. That is, in a conventional configuration, the device configuration is that the radiation source 3, the phase grating 5, and the FPD 4 are placed in predetermined positions. The positional relationship of these parts is determined as follows. Initially, the distance between the phase grating 5 and the FPD 4 is set to the Talbot distance. Otherwise the self-image does not appear on the detection surface of the FPD 4. Further, it is necessary that the self-image be magnified with reference to the phase grating 5 to some extent. Otherwise, the self-image is too fine to be detected with the FPD 4. According to the present invention, attention is paid to the findings that there is no need to set the distance between the phase grating 5 and the FPD 4 to the Talbot distance. However, unless the self-image is not sufficiently magnified with respect to the phase grating 5, the self-image cannot be detected in the same manner as in a conventional configuration. The degree on how the self-image is magnified on the FPD 4 with respect to the original phase grating 5 is determined by a magnification ratio X2/X1. Therefore, in the present invention, the magnification ratio is set to be the same as the magnification ratio in a conventional configuration. With this, even if the distance X2 is reduced, a situation in which the self-image cannot be detected by the FPD 4 due to the excessively small size thereof does not occur. As the distance X2 decrease, the distance X1 also decreases accordingly. This is because the magnification ratio X2/X1 is the same as that of the conventional configuration.

Figure 8:
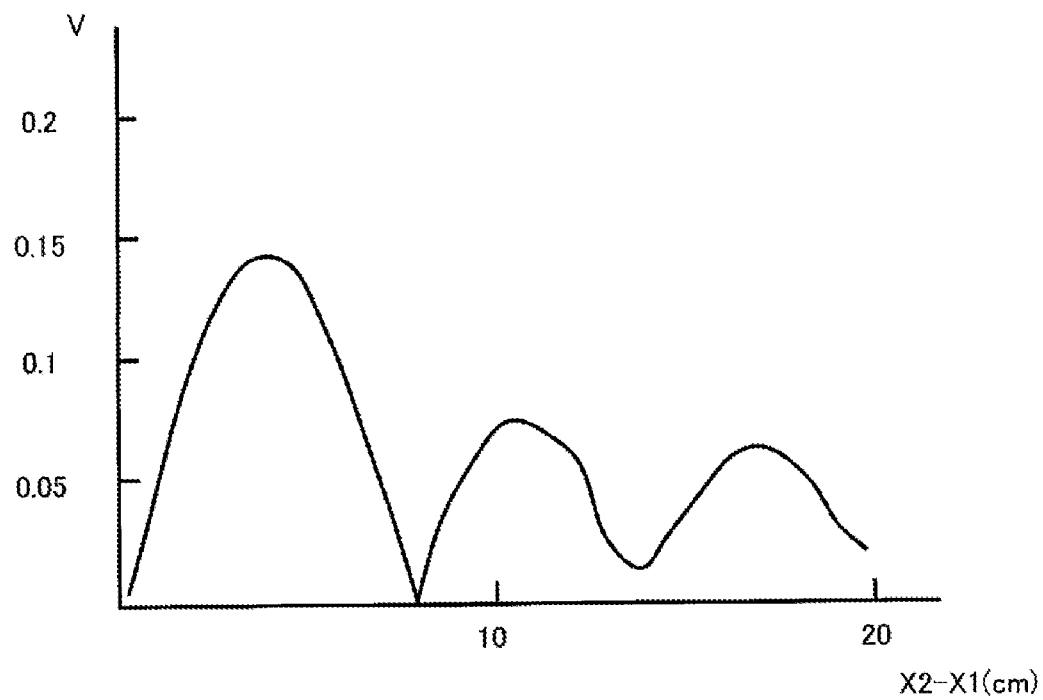
FIG. 8 is a graph showing a relationship between a Talbot distance and visibility according to Example 1.

FIG. 8 shows a simulation result of examining the influence of shifting the distance X2−X1 from the Talbot distance. In this simulation, it is calculated on the premise that the radiation source 3 configured to output X-rays of a certain wavelength actually outputs X-rays of various wavelengths in addition to the wavelength. The vertical axis of the graph denotes visibility V, which means sharpness of a self-image. The horizontal axis of the graph denotes the distance X2–X1 from the phase grating 5 to the FPD 4. In order to obtain a clear self-image, it is sufficient to set the distance X2 from the phase grating 5 to the FPD 4 to the distance corresponding to the highest visibility V in the graph. This distance corresponds to the Talbot distance. Looking closely at the graph shown in FIG. 8, it is noticed that the visibility V does not decrease so much even if it is set to make the distance from phase grating 5 to the FPD 4 smaller than the Talbot distance. That is, the distance X2–X1 does not necessarily have to be the Talbot distance.

The self-image generation portion 11 generates a self-image of the phase grating 5 based on the output of the FPD 4. The generated self-image is output to the transparent image generation portion 12. The transparent image generation portion 12 generates a transparent image in which the phase-contrast of the X-rays generated in the subject M is imaged based on the self-image of the phase grating 5.

The self-image generation portion 11 and the transparent image generation portion 12 are realized by a CPU executing each program. Further, these portions may be divided and executed in arithmetic units in charge of these portions.

As described above, according to the present invention, it is possible to provide a radiation phase contrast imaging device with a small device configuration. According to the present invention, we drew attention to the findings that there is no need to set the distance X2–X1 to the Talbot distance. The distance between the radiation source 3 and the FPD 4 can be set more freely. However, a self-image cannot be detected unless the self-image is sufficiently magnified with respect to the phase grating 5. The degree on how much the self-image is magnified on the FPD 4 with respect to the original phase grating 5 is determined by a magnification ratio X2/X1. Therefore, in the present invention, the magnification ratio is set to be the same as the magnification ratio in a conventional configuration. With this, even if the distance X2 between the radiation source 3 and the FPD 4 is reduced, a situation in which the self-image cannot be detected by the FPD 4 due to the excessively small size thereof does not occur.

That is, there is a relationship P1 (X2/X1)=N·Pd between the distance X1 from the multi-slit to the phase grating 5 and the distance X2 from the multi-slit to the FPD 4. Among them, X2/X1 is called a magnification ratio and is an index showing how much the self-image of the phase grating 5 is magnified on the FPD 4.

By determining the magnification ratio X2/X1 so as to satisfy the above expression according to the array pitch P1 of the absorbers in the phase grating 5 and the array pitch Pd of the detection elements arranged on the detection surface 4a of the FPD 4 and, based on this, determining X2 and X1, the array pitch of the dark lines configuring the self-image can be an integer multiple of the array pitch of the detection elements of the FPD 4. Accordingly, a radiation phase contrast imaging device capable of assuredly detecting a self-image can be provided. Even in cases where the magnification ratio X2/X1 is set to be constant, by reducing the distance X1, the distance X2 can be reduced. This makes it possible to reduce the FPD 4. Further, the device configuration of the radiation phase contrast imaging device can also be reduced.

The present invention is not limited to the aforementioned configuration, and may be modified as follows.

(1) Nothing is provided on the detection surface 4a of the FPD 4 according to Example 1, but the present invention is not limited to this configuration. An absorption grating may be provided on the detection surface 4a of the FPD 4.

(2) According to the above-described Example, the radiation source 3 is configured to irradiate plural types of radiation having different wavelengths, but the present invention is not limited to this configuration. The present invention can also be applied to a radiation source 3 which irradiates monochromatic light radiation.

(3) In the above-described Example, in a device configuration in which the distance X2–X1 is set to a Talbot distance, the magnification ratio X2/X1 indicating how much the self-image of the grating that appears at the detection portion is magnified with respect to the grating, but the present invention is not limited to this configuration. The description of Example shows an ideal state, and it is also possible to adopt a configuration in which the X2/X1 slightly deviates from the device configuration relating to the Talbot distance. When the X2/X1 slightly deviates from the ideal state, the self-image of the phase grating 5 is magnified or reduced on the FPD 4. As a result, the state as shown in FIG. 6 where all the dark lines of the self-image are arranged at the center of the detection element collapses and the dark line of the self-image deviates from the center of the detection element. The most intense deviation of this dark line occurs at the edge portion of the self-image (the edge portion in the orthogonal direction of the dark line). In the present invention, X2–X1 may be set to the magnification rate between from an upper limit magnification ratio in which a stripe patterned dark line configuring the self-image is magnified by ½ of a width of a detection element at an end portion of the self-image in which a positional deviation becomes largest due to a variation of the magnification ratio to a lower limit magnification ratio in which the dark line is narrowed by the ½ of the width of the detection element. Even if X2/X1 is not exactly set to an ideal value, the effects of the present invention will not be impaired and the influence does not appear much in capturing a self-image.

DESCRIPTION OF REFERENCE SYMBOLS 3 radiation source
3b multi-slit
4 FPD (detection portion)
5 phase grating (grating)

The invention claimed is:
1. A radiation phase contrast imaging device comprising:
a radiation source configured to irradiate radiation;
a grating in which absorbers extending in one direction configured to absorb the radiation are arranged in a direction orthogonal to the one direction; and
a detecting portion configured to detect a self-image of the grating caused by a Talbot interference at a detection surface for detecting the radiation,
wherein when a distance from the radiation source to the detection portion is X2 and a distance from the radiation source to the grating is X1, X2–X1 is set to a distance shorter than a Talbot distance in a state in which a magnification ratio X2/X1 showing how much the self-image of the grating which appears at the detection portion in a device configuration in which X2–X1 is set to the Talbot distance is magnified with respect to the grating is maintained constant.

2. The radiation phase contrast imaging device as recited in claim 1, wherein the distance X1 from the radiation source to the grating and the distance X2 from the radiation source to the detection portion satisfy a relationship of:

$$P1(X2/X1)=N \cdot Pd$$

where N is an integer, P1 is an array pitch of the absorber in the grating, and Pd is an array pitch of the detection element arranged on the detection surface of the detection portion.

3. The radiation phase contrast imaging device as recited in claim 1,
wherein no absorption grating is provided between the grating and the detection portion.

4. A radiation phase contrast imaging device comprising:
a radiation source configured to irradiate radiation;
a grating in which absorbers extending in one direction configured to absorb the radiation are arranged in a direction orthogonal to the one direction; and
a detecting portion configured to detect a self-image of the grating caused by a Talbot interference at a detection surface for detecting the radiation,
wherein when a distance from the radiation source to the detection portion is X2 and a distance from the radiation source to the grating is X1, X2−X1 is set to a distance shorter than a Talbot distance by setting a magnification ratio X2/X1 showing how much the self-image of the grating which appears in the detection portion in a device configuration in which X2−X1 is set to a Talbot distance is magnified with respect to the grating to a magnification ratio between from an upper limit magnification ratio in which a stripe patterned dark line configuring the self-image is magnified by ½ of a width of a detection element arrayed in the detection portion at an end portion of the self-image in which a positional deviation becomes largest due to a variation of the magnification ratio to a lower limit magnification ratio in which the dark line is narrowed by the ½ of the width of the detection element.

5. The radiation phase contrast imaging device as recited in claim 4,
wherein the distance X1 from the radiation source to the grating and the distance X2 from the radiation source to the detection portion satisfy a relationship of:

$$P1(X2/X1)=N \cdot Pd$$

where N is an integer, P1 is an array pitch of the absorber in the grating, and Pd is an array pitch of the detection element arranged on the detection surface of the detection portion.

6. The radiation phase contrast imaging device as recited in claim 4,
wherein no absorption grating is provided between the grating and the detection portion.

7. A radiation phase contrast imaging device comprising:
a radiation source configured to irradiate radiation;
a grating in which absorbers extending in one direction configured to absorb the radiation are arranged side by side in a direction orthogonal to the one direction, the grating configured to receive radiation from the radiation source and cause a Talbot interference of the radiation received from the radiation source; and
a detector configured to detect a self-image of the grating resulting from the Talbot interference,
wherein a radiation path extends from the radiation source to the detector,
wherein a distance from a first location in the radiation path to the detector is X2 and a distance from the first location in the radiation path to the grating is X1,
wherein a magnification ratio of the self image at the detector is X2/X1, and
wherein X2−X1 is a distance shorter than the Talbot distance.

8. The radiation phase contrast imaging device of claim 7, wherein the first location in the radiation path corresponds to a location of the radiation source.

9. The radiation phase contrast imaging device of claim 7, further comprising a multi-slit provided in the radiation path between the radiation source and the grating,
wherein the first location in the radiation path corresponds to a location of the multi-slit.

10. The radiation phase contrast imaging device as recited in claim 7,
wherein the distance X1 from the radiation source to the grating and the distance X2 from the radiation source to the detector satisfy a relationship of:

$$P1(X2/X1)=N \cdot Pd$$

where N is an integer, P1 is an array pitch of the absorber in the grating, and Pd is an array pitch of detection elements of the detector.

11. The radiation phase contrast imaging device as recited in claim 7,
wherein no absorption grating is provided between the grating and the detector.

* * * * *